US012599717B2

(12) United States Patent
Yang

(10) Patent No.:   US 12,599,717 B2
(45) Date of Patent:      Apr. 14, 2026

(54) UNILATERALLY DRIVEN DRUG INFUSION DEVICE

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 613 days.

(21) Appl. No.: 18/024,278

(22) PCT Filed: Jul. 15, 2021

(86) PCT No.: PCT/CN2021/106456
§ 371 (c)(1),
(2) Date: Mar. 2, 2023

(87) PCT Pub. No.: WO2022/052621
PCT Pub. Date: Mar. 17, 2022

(65) Prior Publication Data
US 2023/0256162 A1      Aug. 17, 2023

(51) Int. Cl.
A61M 5/142          (2006.01)
A61M 5/145          (2006.01)
(Continued)

(52) U.S. Cl.
CPC ...... A61M 5/14248 (2013.01); A61M 5/1452 (2013.01); A61M 5/158 (2013.01); (Continued)

(58) Field of Classification Search
None
See application file for complete search history.

(56) References Cited

U.S. PATENT DOCUMENTS

| | | | |
|---|---|---|---|
| 2003/0236498 A1 | 12/2003 | Gross et al. | |
| 2009/0105650 A1 | 4/2009 | Wiegel et al. | |
| 2019/0117881 A1* | 4/2019 | Yang ................. | A61M 5/16804 |

FOREIGN PATENT DOCUMENTS

| | | |
|---|---|---|
| CN | 103007381 | 4/2013 |
| CN | 106110445 | 11/2016 |

(Continued)

OTHER PUBLICATIONS

"International Search Report (Form PCT/ISA/210) of PCT/CN2021/106456," mailed on Oct. 14, 2021, with English translation thereof, pp. 1-5.

*Primary Examiner* — Manuel A Mendez
(74) *Attorney, Agent, or Firm* — JCIP GLOBAL INC.

(57)          ABSTRACT

A unilaterally driven drug infusion device includes: a reservoir, a piston and a screw, the piston connected with the screw and arranged in the reservoir; a driving unit including rotating shaft and driving member, and the driving member including driving end; driving wheel provided with wheel teeth; a linear actuator and a reset unit respectively connected to the driving member; and at least two blocking walls, arranged at one side of the driving unit to limit the advancing position of the driving unit. The infusion device is able to precisely control the rotation amplitude of the driving member and improve the infusion accuracy of the infusion device. The user or the closed-loop system is able to flexibly select different infusion modes to precisely control the body fluid level to meet the needs of the body, improving user experience.

14 Claims, 9 Drawing Sheets

(51) Int. Cl.
    *A61M 5/158*       (2006.01)
    *A61M 5/168*       (2006.01)
    *A61M 5/172*       (2006.01)

(52) U.S. Cl.
    CPC ...... *A61M 5/1684* (2013.01); *A61M 5/16877* (2013.01); *A61M 5/172* (2013.01); *A61B 2560/0209* (2013.01); *A61M 2005/14208* (2013.01); *A61M 2005/14252* (2013.01); *A61M 2005/14268* (2013.01); *A61M 2005/14533* (2013.01); *A61M 2205/0266* (2013.01); *A61M 2205/106* (2013.01); *A61M 2205/50* (2013.01)

(56) References Cited

FOREIGN PATENT DOCUMENTS

| | | | | |
|---|---|---|---|---|
| CN | 106139311 | 11/2016 | | |
| CN | 111939371 | 11/2020 | | |
| CN | 112237660 | 1/2021 | | |
| CN | 112295061 | 2/2021 | | |
| CN | 112295062 | 2/2021 | | |
| EP | 1874390 B1 * | 10/2014 | .......... | A61M 5/1452 |
| WO | 2020233128 | 11/2020 | | |
| WO | 2021012622 | 1/2021 | | |
| WO | 2021012623 | 1/2021 | | |
| WO | 2021012853 | 1/2021 | | |
| WO | 2021017408 | 2/2021 | | |

* cited by examiner

Front end of
driving end

UNILATERALLY DRIVEN DRUG INFUSION DEVICE

CROSS-REFERENCE TO RELATED APPLICATION

This application is a 371 of international application of PCT application serial no. PCT/CN2021/106456, filed on Jul. 15, 2021, which claims the priority benefit of PCT application no. PCT/CN2020/113980, filed on Sep. 8, 2020. The entirety of each of the above-mentioned patent applications is hereby incorporated by reference herein and made a part of this specification.

TECHNICAL FIELD

The present invention mainly relates to the field of medical instruments, in particular to a unilaterally driven drug infusion device.

BACKGROUND

A drug infusion device can continuously deliver drug into a patient's body for disease treatment. Drug infusion devices are widely used in the field of diabetes treatment, which continuously infuse required dosage of insulin into the patient's subcutaneous tissue, thereby simulating the secretion function of the pancreas to keep the blood glucose stable. The drug fluid is usually stored inside the infusion pump. The existing drug infusion device, controlled by remote device, is usually attached directly on the patient's skin through a medical adhesive tape.

Currently, the infusion accuracy of the existing infusion device is relatively low, and the highest infusion accuracy is limited to the minimal infusion increment (unit infusion amount), which is determined by the advancing increment of the driving wheel. The user or the closed-loop system cannot flexibly choose the infusion mode to meet the body's actual requirements for drugs.

Therefore, the prior art urgently needs a drug infusion device with high infusion accuracy.

BRIEF SUMMARY OF THE INVENTION

The embodiment of the invention discloses a unilaterally driven drug infusion device, provided with at least two blocking walls, can precisely control the rotation amplitude of the driving member and improve the infusion accuracy of the infusion device. The user or the closed-loop system can flexibly select different infusion modes to precisely control the body fluid level to meet the needs of the body.

The invention discloses a unilaterally driven drug infusion device, comprising: a reservoir, a piston and a screw, the piston connected with the screw and arranged in the reservoir; a driving unit including at least one rotating shaft and at least one driving member, and the driving member includes at least one driving end, the driving member can rotate around the rotating shaft to advance or reset the driving end; at least one driving wheel provided with wheel teeth, and the advancing driving end can push the wheel teeth to rotate the driving wheel, thereby driving the screw forward; a linear actuator and a reset unit respectively connected to the driving member, the linear actuator and the reset unit respectively apply driving power to the driving member to advance and reset the driving end; and at least two blocking walls, arranged at one side of the driving unit to limit the advancing position of the driving unit.

According to an aspect of the present invention, the blocking wall is an elastic conductive member.

According to an aspect of the present invention, the elastic conductive member is one or a combination of conductive spring, conductive leaf spring, conductive rubber, or conductive silica gel.

According to an aspect of the present invention, the linear actuator includes an electrically driven linear actuator or an electrically heated linear actuator.

According to one aspect of the present invention, the reset unit includes an electrically driven linear actuator or an electrically heated linear actuator.

According to one aspect of the present invention, at least a blocking wall is arranged on the other side of the driving unit.

According to an aspect of the present invention, it further includes a control unit, jointly control the advancing end of the driving member with the blocking wall on the other side of the driving unit.

According to an aspect of the present invention, the reset unit is an elastic conductive member, the elastic conductive member at least includes one or a combination of a spring, an elastic piece, an elastic plate, an elastic rod, rubber and other elastic members.

According to an aspect of the present invention, the reset unit is an elastic conductive member.

According to an aspect of the present invention, the elastic conductive member includes a metal spring or conductive rubber.

According to an aspect of the present invention, the driving member have a variety of different operating modes, thereby making the infusion device have various different infusion increments or infusion rate.

According to an aspect of the present invention, the driving member have a variety of different operating modes, thereby making the infusion device have various different infusion increments or infusion rates.

According to an aspect of the present invention, the operating mode of the driving member includes the amplitude of the reciprocating movement, frequency of reciprocating movement or the movement rate, therefore a variety of different operating modes of the driving member include different amplitude or frequency of reciprocating movement, or include various different movement rates.

According to an aspect of the present invention, it further includes a base on which the driving wheel is movably assembled, and the base and the driving wheel are frictional fit, and the driving wheel stops rotating when the driving end is sliding on the surface of the wheel teeth.

According to an aspect of the present invention, it further includes a position limited member which is movably assembled on the base to limit the position of the driving wheel, and the position limited member and the driving wheel are frictional fit, and the driving wheel stops rotating when the driving end is sliding on the surface of the wheel teeth.

Compared with the prior art, the technical solution of the present invention has the following advantages:

In the unilaterally driven drug infusion device disclosed in the present invention, provided with at least two blocking walls, can precisely control the rotation amplitude of the driving member and improve the infusion accuracy of the infusion device. The user or the closed-loop system can flexibly select different infusion modes to precisely control the body fluid level to meet the needs of the body, improving user experience.

Furthermore, the reset unit includes an electrically driven linear actuator, an electrically heated linear actuator, or an elastic member. The magnitude of the driving power output by the linear actuator can be controlled by the current, therefore the power output is more stable, thus making the amplitude or rate of movement of the driving member more stable and controllable. In addition, when the reset unit is an elastic member, the driving member can be automatically reset without consuming electric energy, thereby reducing the power consumption and cost of the infusion device.

Furthermore, the driving member has a variety of different operating modes, thereby making the infusion device have various different infusion increments or infusion rates. When the infusion device has a variety of different infusion increments or infusion rates, the user or closed-loop system can arbitrarily choose the appropriate infusion mode to accurately control the level of body fluids according to the actual requirements of the body, further improving the user experience.

Furthermore, the infusion device further includes a base which is frictional fit with the driving wheel. The driving wheel stops rotating when the driving end is sliding on the surface of the wheel teeth, improving the accuracy of drug infusion and eliminating potential safety hazards.

Furthermore, the infusion device further includes a position limited member which is movably assembled on the base to limit the position of the driving wheel. The position limited member can make full use of the internal space of the infusion device, and frictionally cooperate with the driving wheel at multiple positions.

4

Figure 11A:
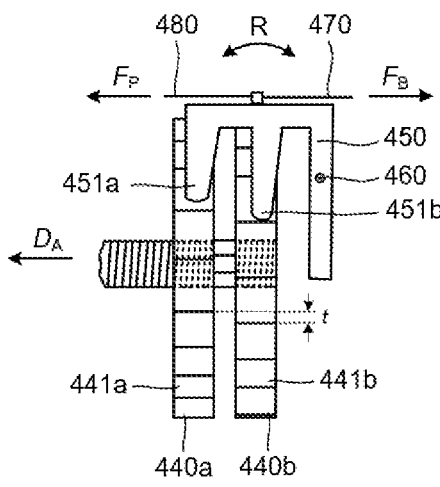
Figure 11B:
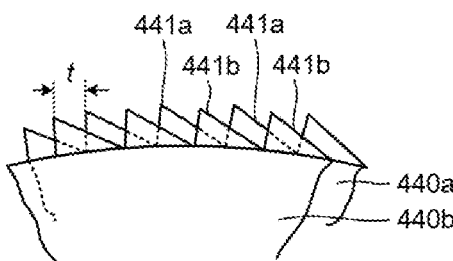
Figure 12A:
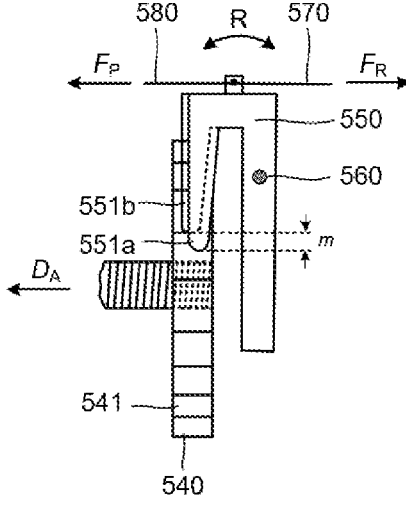
Figure 12B:
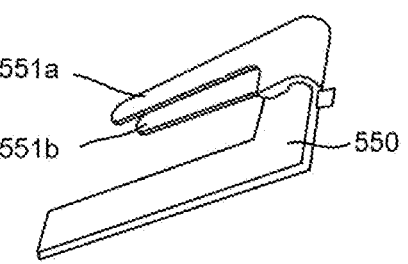

FIG. 11*a* and FIG. 11*b* are schematic diagrams of two driving ends of a driving member cooperating with two driving wheels, respectively according to yet another embodiment of the present invention;

FIG. 12*a* and FIG. 12*b* are schematic diagrams of the driving member includes two driving ends disposed up and down according to yet another embodiment of the present invention.

DETAILED DESCRIPTION

As mentioned above, the infusion accuracy of the existing infusion device is relatively low, and the highest infusion accuracy is limited to the minimal infusion increment (unit infusion amount) which is determined by the advancing increment of the driving wheel. The user or the closed-loop system cannot flexibly choose the infusion mode to meet the body's actual requirements for drugs.

In order to solve this problem, the present invention provides a unilaterally driven drug infusion device. The infusion device is provided with at least two blocking walls, can precisely control the rotation amplitude of the driving member and improve the infusion accuracy of the infusion device. The user or the closed-loop system can flexibly select different infusion modes to precisely control the body fluid level to meet the needs of the body.

Various exemplary embodiments of the present invention will now be described in detail with reference to the drawings. The relative arrangement of the members and the steps, numerical expressions and numerical values set forth in the embodiments are not to be construed as limiting the scope of the invention.

In addition, it should be understood that, for ease of description, the dimensions of the various members shown in the figures are not necessarily drawn in the actual scale relationship, for example, the thickness, width, length or distance of certain units may be exaggerated relative to other components.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in following description of the drawings.

Figure 1A:
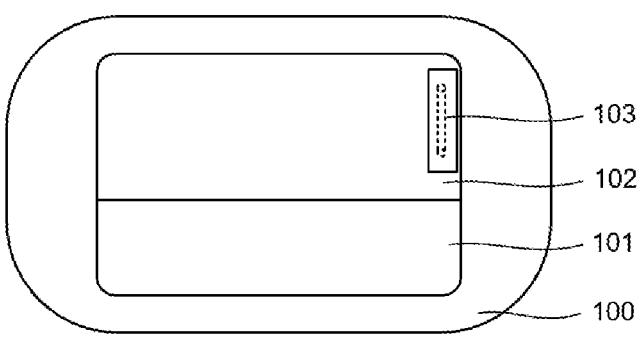
FIG. 1*a* and FIG. 1*b* are schematic top views of a unilateral driven drug infusion device, respectively, according to two different embodiments of the present invention.
Figure 1B:
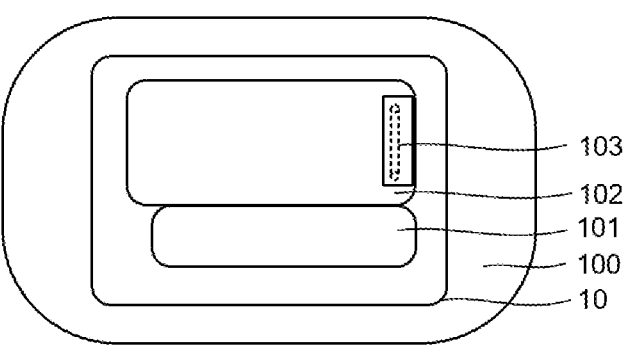

FIG. 1*a* and FIG. 1*b* are schematic top views of a unilateral driven drug infusion device, respectively, according to two different embodiments of the present invention.

The unilateral driven drug infusion device includes an adhesive patch 100, control unit 101, infusion unit 102 and infusion needle 103.

The control unit 101 is used to control the driving power output by the linear actuator or by the reset unit inside the infusion unit 102 to control the drug infusion. The control unit 101 can also establish wireless communication with a remote device, and the like.

The infusion unit 102 includes various units for realizing the function for drug infusion, which will be described in detail below.

In the embodiment of the present invention, the control unit 101 and the infusion unit 102 are designed separately and connected by a waterproof plug. The control unit 101 can be reused, while the infusion unit 102 can be discarded after a single use. In another embodiment of the present invention, the infusion unit 102 and the control unit 101 are disposed inside the same housing 10 and connected by a wire, which both units will be discarded together after a single use, as shown in FIG. 1b.

The adhesive patch 100 is used to attach the infusion unit 102 or the control unit 101, or both of them as a whole to the host skin surface.

One end of the infusion needle 103 is connected to the outlet of the reservoir, while the other end pierces the skin to infuse the drug subcutaneously. In the embodiment of the present invention, the infusion needle 103 is disposed at one end of the infusion unit 102. In other embodiments of the present invention, the infusion needle 103 may be disposed at other positions according to its functions or structural features of the device, such as being disposed at the middle portion of the device, which is not specifically limited herein. The infusion needle 103 is a rigid infusion needle or a flexible infusion needle, or designed according to its different positions and functions, the design of infusion needle 103 can also adopt a combination of rigid infusion needle(s) and flexible infusion needle(s), which is not specifically limited herein. Preferably, in the embodiment of the present invention, the infusion needle 103 is a rigid infusion needle.

Figure 2:
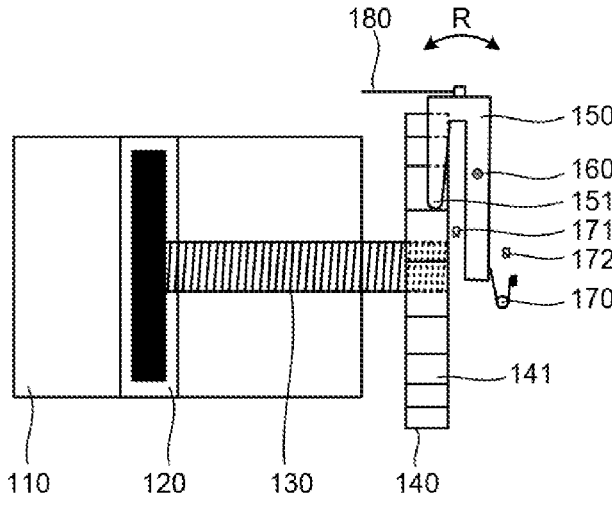
FIG. 2 is a schematic diagram of main components in the infusion unit according to an embodiment of the present invention.

FIG. 2 is a schematic diagram of main components in the infusion unit 102 according to an embodiment of the present invention.

The internal component of the infusion unit 102 mainly includes at least a reservoir 110, a piston 120, a screw 130, a driving wheel 140, a driving unit (not shown), a reset unit 170 and a linear actuator 180. The driving unit includes at least one driving member 150 and at least one rotating shaft 160. In the embodiment of this present invention, the driving member 150 is connected to the reset unit 170 and the linear actuator 180, respectively. It should be noted that the connection herein includes mechanical connection or electrical connection.

The reservoir 110 is used for storing liquid drug. Drugs include, but are not limited to, insulin, glucagon, antibiotics, nutrient solutions, analgesics, morphine, anticoagulants, gene therapy drugs, cardiovascular drugs or chemotherapy drugs, etc.

The piston 120 is used to infuse liquid drug into the body.

The screw 130 is connected to the piston 120 and the driving wheel 140, respectively. In the embodiment of the present invention, the driving wheel 140 advances the screw 130 forward by screwing, the screw 130 then forces the piston 120, arranged in the reservoir 110, to move forward, so as to achieve the purpose of drug infusion. When the screw 130 is a flexible screw, the screw 130 may be designed to be curved. In one embodiment of the invention, the flexible screw is formed by a plurality of threaded sub-units movably connected one by one.

The peripheral surface of the driving wheel 140 is provided with wheel teeth 141. The wheel teeth 141 are gear teeth or ratchet teeth. Specifically, in the embodiment of the present invention, for improving driving efficiency, the wheel teeth 141 are ratchet teeth which can be pushed more easily.

One driving end 151 is provided on the driving member 150 to push the wheel teeth 141, thereby rotating the driving wheel 140. The driving member 150 is movably connected to the rotating shaft 160.

The linear actuator 180 and the reset unit 170 cooperate with each other to make the driving member 150 rotate reciprocally around the rotating shaft 160, as shown in the R direction in FIG. 2, thereby making the driving end 151 move in the advancing direction and reset direction. When the driving member 150 performs one reciprocating rotation, the driving end 151 drives the driving wheel 140 forward one tooth, the driving wheel 140 drives the screw 130 forward one step, and the screw 130 engages the piston 120 to infuse one unit of drug.

It should be noted here that the advancing direction of the driving end 151 refers to the direction in which the wheel teeth 141 moves, while the reset direction of the driving end 151 is opposite to the advancing direction. During reset, the driving end 151 only slides on the surface of the wheel teeth 141 without pushing.

In some embodiments of the present invention, the reset unit 170 at least includes a spring, an elastic piece, an elastic plate, an elastic rod, rubber and other elastic members. It should be noted that the spring herein includes a compression spring, an extension spring, or a torsion spring, etc, so as to the meaning of the spring below. Specifically, in the embodiment of the present invention, the reset unit 170 is a torsion spring which is more conducive to the reset of the driving member 150. In some embodiments of the present invention, the reset unit 170 may also be an elastic conductive member, such as a metal spring, conductive rubber, or the like. In other embodiments of the present invention, the reset unit 170 includes an electrically driven linear actuator or an electrically heated linear actuator, such as a shape memory alloy. The type, material selection or the position of the reset unit 170 are not specifically limited herein, as long as it can satisfy the condition of making the driving member 150 rotate in the reset direction.

After being energized, the physical form of the material of the linear actuator, like shape memory alloy, changes, which makes shrinkage deformation of the shape memory alloy occur, thereby outputting the driving power. The higher the current is, the larger the shrinkage deformation of the shape memory alloy occurs, and the greater the driving power outputs. Obviously, when the current is constant, the amplitude of the driving power output by the shape memory alloy is also constant, therefore the shape memory alloy can output stable and controllable driving power for drug infusion.

The linear actuator 180 is an electrically driven linear actuator or an electrically heated linear actuator. By alternately turning on and off, the linear actuator 180 outputs power in pulses. Specifically, in the embodiment of the present invention, the linear actuator 180 is a shape memory alloy.

Figure 3A:
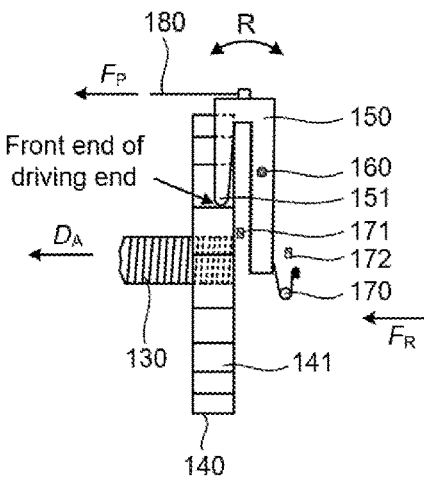
FIG. 3*a*-FIG. 3*c* are top views of the driving end pushing the wheel teeth according to different embodiments of the present invention.
Figure 3B:
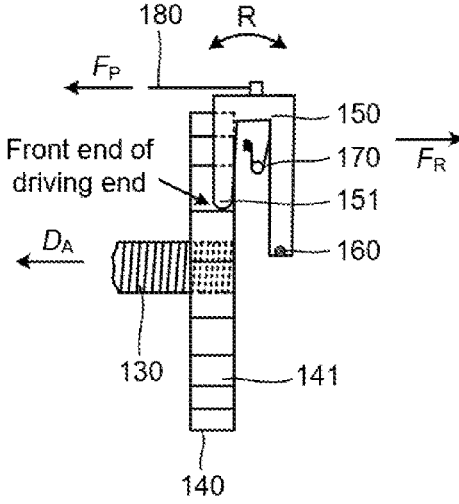
Figure 3C:
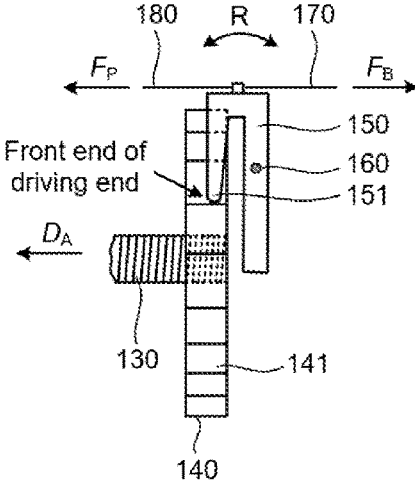
Figure 4A:
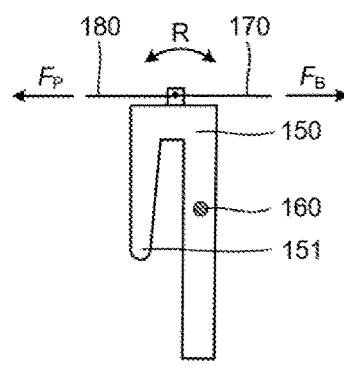
FIG. 4*a*-FIG. 4*c* are schematic diagrams of the linear actuator, the reset unit and the driving member cooperating with each other according to different embodiments of the present invention.
Figure 4B:
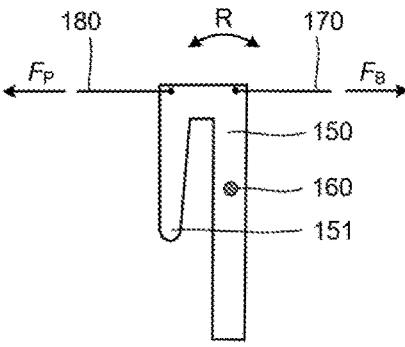
Figure 4C:
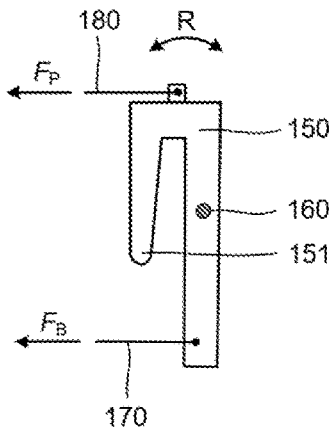

FIG. 3a-FIG. 3c are top views of the driving end 151 pushing the wheel teeth 141 in different embodiments of the present invention. FIG. 4a-FIG. 4c are schematic diagrams of the linear actuator 180, the reset unit 170 and the driving member 150 cooperating with each other in different embodiments of the present invention.

As shown in FIG. 3a and FIG. 3b, the principle of the reciprocating rotation of the driving member 150 in the embodiment of the present invention is as follows. When the linear actuator 180 pulls the driving member 150 by force $F_P$, the driving member 150 rotates counter-clockwise (advancing direction) around the rotating shaft 160, driving the driving end 151 to push the wheel teeth 141 forward, and thereby making the driving wheel 140 rotate. The driving wheel 140 then moves the screw 130 forward in $D_A$ direction. The reset unit 170, an elastic member, builds a gradually increasing elastic force $F_R$. When the linear actuator 180 stops applying force and under the action of only the elastic force $F_R$, the driving member 150 will rotate clockwise (reset direction) around the rotating shaft 160. At this time, the driving end 151 just slides on the surface of the wheel teeth 141 instead of pushing them, therefore the driving wheel 140 stops rotating. The driving member 150 completes one reciprocating rotation.

As shown in FIG. 3b, in another embodiment of the present invention, the reset unit 170 and the linear actuator 180 are disposed on the same side of the rotating shaft 160. And according to the general technical principles, those skilled in the art can arbitrarily adjust the positional relationship and the connection relationship of the reset unit 170, the driving member 150, and the linear actuator 180, which is not specifically limited herein, as long as the above-mentioned rotation processes can be achieved.

As shown in FIG. 3c, in yet another embodiment of the present invention, the reset unit 170 includes an electrically driven linear actuator or an electrically heated linear actuator, such as a shape memory alloy. Although the technical principle that the driving end 151 pushes the wheel teeth 141 is consistent with the foregoing, the driving member 150 cannot automatically reset after the driving end 151 stops advancing, therefore, the reset unit 170 is required to provide the reset force $F_B$ whose direction is opposite with that of $F_P$, thereby making the driving member 150 rotate reciprocally with the cooperation of the reset unit 170 and the linear actuator 180. Obviously, those skilled in the art can arbitrarily adjust the directions of the $F_P$ and $F_B$ as needed, as long as the conditions for reciprocating rotation of the driving member 150 are satisfied, as shown in FIG. 4a-FIG. 4c.

Preferably, as shown in FIG. 3a to FIG. 3c, in the embodiment of the present invention, the directions of $F_P$, $F_R$ (or $F_B$) and $D_A$ are parallel to one another. This parallel design can make full use of space and optimize the structural relationships inside the infusion device, making internal design more compact.

In other embodiments of the present invention, the $F_P$ direction, the $F_R$ (or $F_B$) direction, or the $D_A$ direction may not be parallel, which is not specifically limited herein, as long as the purpose of making the driving member 150 rotate reciprocally can be achieved.

Figure 5A:
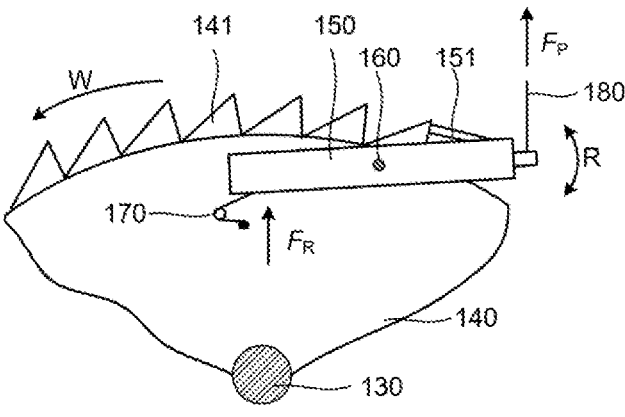
FIG. 5*a*-FIG. 5*b* are schematic diagrams of that the pulling direction of the linear actuator is not parallel to the advancing direction of the screw according to another embodiment of the present invention.
Figure 5B:
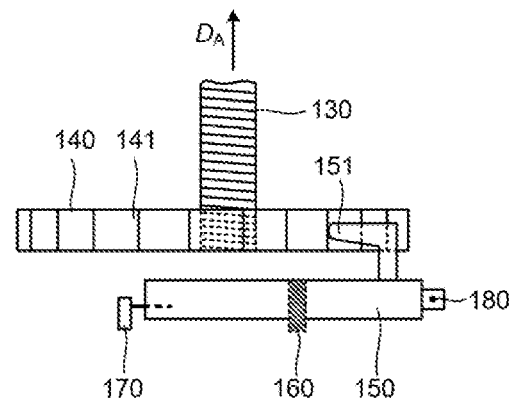

FIG. 5a-FIG. 5b are schematic diagrams of that the pulling direction of the linear actuator 180 is not parallel to the advancing direction of the screw 130. FIG. 5b is a top view of FIG. 5a.

The $F_P$ direction of the linear actuator 180 is perpendicular to the forward direction $D_A$ of the screw 130. The rotating shaft 160 and the reset unit 170 are disposed on the base 190. As described above, the driving member 150, rotating reciprocally in the R direction, drives the driving end 151 to push the wheel teeth 141, making the driving wheel 140 rotate in the W direction and driving the screw 130 to advance in the $D_A$ direction. The driving principle of the driving member 150 is consistent with the foregoing embodiment.

Figure 6A:
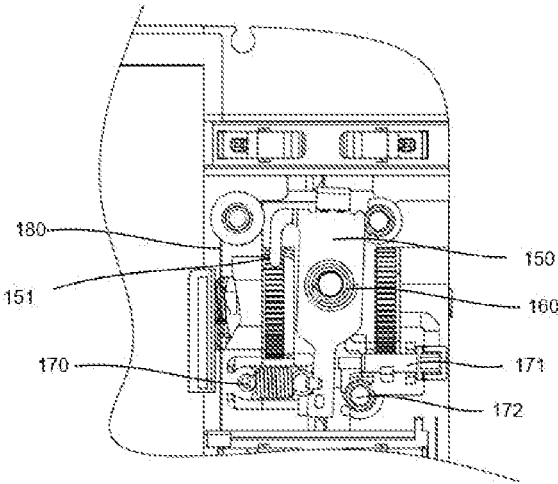
FIG. 6*a*-FIG. 6*c* are schematic diagrams of the driving member at the initial position, half-way position and full-way position according to an embodiment of the present invention.
Figure 6B:
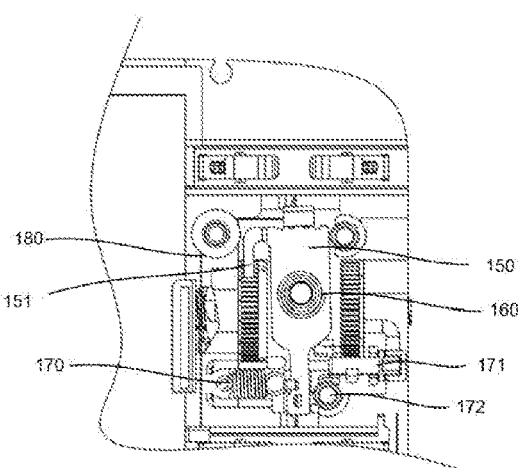
Figure 6C:
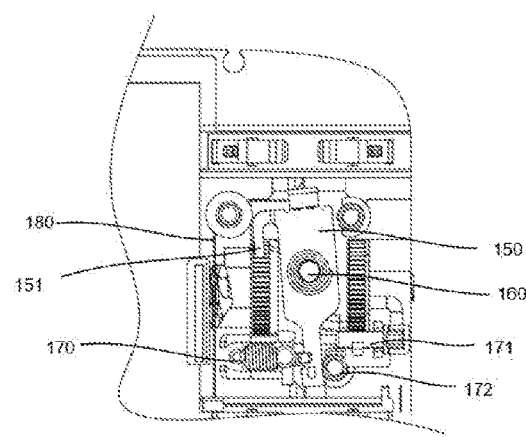

FIG. 6a-FIG. 6c are schematic diagrams of the driving member at the initial position, half-way position and full-way position according to an embodiment of the present invention.

In the embodiment of the present invention, blocking walls 171 and 172 that can limit the advancing position of the driving member 150 are also provided in the infusion device, and blocking wall 171 is a half-way blocking wall, blocking wall 172 is a full-way blocking wall. When the driving member 150 is in the initial position, the driving member 150 is not contacted with the blocking wall. When the driving member 150 is in the half-way position, the driving member 150 is contacted with the blocking wall 171. When the driving member 150 is in the full-way position, the driving member 150 is contacted with the blocking wall 172. When the driving component 150 is contacted with the retaining wall 171 or 172, the electric potential of the contact point is changed, triggering an electrical signal, which will be transmitted to the control unit 101 through a wire. The control unit 101 determines whether the drive unit has reached the advancing end of the selected infusion mode. In the embodiment of the present invention, the driving wheel 140 drives the screw 130 forward one step, one unit of drug (unit infusion amount) infused by the infusion device, thus, in one reciprocating rotation, when the advancing end of the driving unit is the contact point between the driving unit and the half-way blocking wall 171, ½ unit infusion amount can be infused, and the infusion devise can precisely control the rotation amplitude of the driving member 150, improve the infusion accuracy of the infusion device and meet the requirements of users or patients for different infusion accuracy.

Preferably, a first electrical signal is triggered when the linear actuator 180 pulls the driving member 150 forward and contact with the half-way blocking wall 171, and the driving end 151 pushes the driving wheel 140 forward ½ tooth, and the drive wheel 140 drives the screw 130 forward ½ step, the first electrical signal is transmitted to the control unit 101 to determine whether the drive unit has reached the advancing end of the selected infusion mode. When the highest accuracy requirement is ½ unit infusion amount in the selected infusion mode, the control unit 101 controls the linear actuator 180 to stop the power output, and the drive unit resets under the action of the reset unit; When the highest accuracy requirement is 1 unit infusion amount in the selected infusion mode, the control unit 101 controls the linear driver 180 to continue to output power, and when the linear actuator 180 pulls the driving member 150 to continue to move forward, a second electrical signal is triggered when the linear actuator 180 pulls the driving member 150 forward, compress the half-way blocking wall 171 and contact the full-way blocking wall 172, the drive end 151 pushes the drive wheel 140 forward another ½ tooth, the drive wheel 140 drives the screw 130 forward another ½ step, the control unit 101 controls the linear drive 180 to stop the power output, and the drive unit resets under the action of the reset unit.

In the embodiment of the present invention, for example, when insulin is infused, if the unit infusion amount is 0.001 U, the infusion amount of 0.0005 U and 0.001 U can be completed in one reciprocating movement. Correspondingly, when the requirement of the selected infusion mode is 0.0015 U, the infusion can be completed by one full reciprocating movement and a half reciprocating rotation of the driving unit. Of course, when the requirement of selected infusion mode is 0.001 U*n+0.0005 U, the infusion can be completed by n times full reciprocating rotation and a half reciprocating rotation of the driving unit.

In another embodiment of the present invention, the number of blocking walls can also be three, namely, ⅓-way blocking wall, ⅔-way blocking wall, and full-way blocking wall, respectively. Correspondingly, ⅓ unit infusion amount can be infused in one infusion process, and the rotation amplitude of the driving member 150 can be further accurately controlled, the infusion accuracy can be improved, and the requirements of users or patients for different infusion accuracy can be met. Similarly, the number of blocking walls can also be 4 or more (n≥4). Correspondingly, the infusion accuracy can be increased to 1/n unit infusion amount. Theoretically, greater n, higher infusion accuracy, it can meet more requirements of different users or patients for different infusion accuracy. However, due to the requirement of miniaturization of the infusion device, too many blocking walls will increase the size and the design difficulty of the infusion device, therefore, 2-3 blocking walls will be better.

In the embodiment of the present invention, the blocking walls 171 and 172 are arranged on the same side of the driving unit, the reset unit 170 is an elastic member or an elastic conductive member, the other side of the driving unit is not provided with a blocking wall, and the advancing end of the driving member 150 on the other side is determined by the reset unit, or one or two blocking walls can be provided on the other side of the driving unit, and the advancing end of the driving member 150 on the other side is determined by the reset unit and the blocking wall.

In another embodiment of the present invention, the reset unit 170 is an electrically driven linear actuator or an electrically heated linear actuator, such as a shape memory alloy, and the blocking walls 171 and 172 are arranged on the same side of the driving unit, two blocking walls are correspondingly provided on the side of the driving unit to limit the advancing end of the driving member 150. Alternatively, it is also possible to provide only one blocking wall on the other side of the driving unit, and the advancing end of the driving member 150 on the other side is controlled by the control unit 101 and the blocking wall, or no blocking wall provided on the other side of the driving unit, the advancing end of the driving member 150 on the other side is totally controlled by the control unit 101.

Similarly, in the embodiment of the present invention, when the number of blocking walls on one side of the drive unit is more than two, the number of the blocking wall provided on the other side of the driving unit is not specifically limited here, as long as advancing end of the drive member 150 can be controlled.

In the embodiment of the present invention, the blocking wall is one or a combination of conductive spring, conductive leaf spring, conductive rubber, or conductive silica gel etc., preferably, in the embodiment of the present invention, the blocking wall is a POGO pin, and the blocking wall 171 is arranged along the horizontal direction (paralleled to the screw), and the blocking wall 172 is arranged in the vertical direction (perpendicular to the bottom of the infusion device), which can make full use of the internal space of the infusion device and optimize the design of the infusion device. The blocking wall 171 is arranged closer to the driving unit than the blocking wall 172, the driving unit can smoothly and sequentially contact with blocking wall 171 and blocking wall 171 to determine the advancing end of the driving member 150, and trigger the electrical signals to realize the high-accuracy delivery of the infusion device. In other embodiments of the present invention, the design, material and arrangement of each blocking wall are not specifically limited here, as long as it can contact with the driving unit to determine the advancing end of the driving member 150, and trigger the electrical signals to realize high-accuracy delivery of the infusion device.

Figure 7:
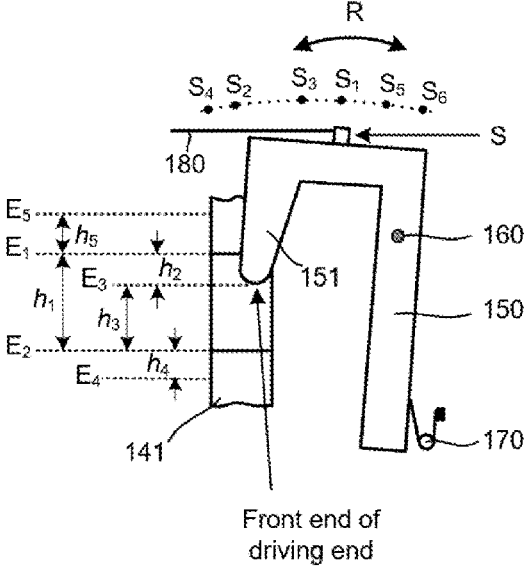
FIG. 7 is a schematic diagram of the reciprocating rotation amplitude of the driving member according to an embodiment of the present invention.

FIG. 7 is a schematic diagram of the reciprocating rotation amplitude of the driving member 150 according to an embodiment of the present invention.

The principle of the driving member 150 implementing two reciprocating rotation amplitudes according to the embodiment of the present invention is as follows. The control module controls the magnitude of the force output of the linear actuator 180, and the reset member 170 implements resetting function, which makes the driving member 150 to reciprocate, making the driving end 151 advance or reset. $E_n$ represents the position reached by the front end of the driving end, such as $E_1$, $E_2$, $E_3$, $E_4$, and $E_5$. $h_n$ represents the distance between two different positions $E_n$. $S_n$ represents the different positions of the point S of the force output by the linear actuator 180 during the reciprocating rotation, and the dotted arc in FIG. 7 represents the trajectory of S, therefore, $S_1$, $S_2$, $S_3$, $S_4$, $S_5$ correspond with $E_1$, $E_2$, $E_3$, $E_4$, $E_5$, respectively. Obviously, the movement distance between different $S_n$ can be used to represent the rotation amplitude of the driving member 150. Specifically, in the embodiment of the present invention, $h_1$ is the pitch of wheel teeth, and $h_1=3h_2$. When the linear actuator 180, according to the instruction, makes the driving end 151 to advance the wheel teeth 141 from the $E_1$ to the $E_2$ position, the linear actuator 180 stops outputting power, and the reset member 170 starts to work until resetting the driving end 151 to the $E_3$ position, which makes the driving member 150 complete the first reciprocating. The rotation amplitude of the driving member 150 is $S_1$-$S_2$ and $S_2$-$S_3$. During the first reciprocating rotation, the front end of the driving end pushes one tooth forward by a distance $h_1$, the drug infusion volume is $V_1$, and its reset distance is $h_3$. At this time, the infusion volume $V_1$ is regarded as the infusion increment in this first mode. When the next driving is performed, the linear actuator 180 outputs force again. During the advancing distance $h_3$, the driving end 151 just slides on the surface of the wheel teeth 141, and the driving wheel 140 does not rotate, nor does the drug infusion of the infusion device implement. When the front end of the driving end reaches the $E_2$ position and continues to advance by a distance of $h_4$, the front end of the driving end pushes the wheel teeth 141 to the $E_4$ position, so the driving wheel 140 rotates, implementing the drug infusion. When the linear actuator 180 stops outputting the force, the reset member 170 resets the driving end 151 to a certain position, such as the $E_5$ position, therefore, the driving member 150 completes the second reciprocating rotation, and the driving member 150 rotates by $S_3$-$S_4$ and $S_4$-$S_5$. During the second reciprocating rotation, the forward distance of the front end of the driving end is $(h_3+h_4)$, and the drug infusion volume is $V_2$. At this time, the infusion volume $V_2$ is the infusion increment in this second mode. Obviously, the driving member 150 only drives the driving wheel 140 to rotate under the rotation amplitudes $S_1$-$S_2$ and $S_2$-$S_4$ in these two modes. For the rotation amplitude $S_1$-$S_2$ is greater than the rotation amplitude $S_2$-$S_4$ (or $h_1>h_4$), $V_1>V_2$. Therefore, the infusion device of the embodiment of the present invention has two different infusion increments.

By analogy, the distance between $E_1$, $E_2$, $E_3$, $E_4$, $E_5$ can be arbitrarily selected, such as $h_1=h_2$, $h_1=2h_2$, $h_1=4h_2$, etc., the infusion device has a variety of different infusion increments. Or the force point S can also reach to the $S_6$ position, and $S_4$ and $S_6$ may not be the limit positions for the rotating of the driving member 150, which is not specifically limited herein.

It should be noted that, as described above, in the embodiment of the present invention, the infusion device does not necessarily implement drug infusion when the driving end 151 advances. Only when the driving end 151 pushes the wheel teeth 141 forward, the infusion device does.

Each rotation amplitude of the driving member 150 corresponds with an infusion increment. Therefore, a variety of different rotation amplitudes of the driving member 150 make the drug infusion device have a variety of different infusion increments. Taking insulin as an example, the infusion increment range of the drug infusion device in the embodiment of the present invention is 0.0005 U~0.25 U (here, the infusion increment range includes endpoint values, that is, the infusion increment includes 0.0005 U and 0.25 U). In some embodiments of the present invention, the infusion increment of the drug infusion device may include 0.001 U, 0.0025 U, 0.005 U, 0.0075 U, 0.01 U, 0.025 U, 0.05 U, 0.075 U, 0.1 U, etc. Specifically, in the embodiment of the present invention, the infusion increment of the drug infusion device includes 0.005 U, 0.0075 U, 0.01 U, 0.025 U, and 0.05 U.

It should be noted that in the embodiment of the present invention, the insulin concentration is 100 U/ml. In other embodiments, the insulin concentration may also be 200 U/ml, 400 U/ml, etc., which is not specifically limited here.

It should be noted here that when $h_1=h_2$, the infusion increment of the infusion device always maintains $V_1$ with the rotation amplitude always maintaining $S_1\text{-}S_2$ and $S_2\text{-}S_1$, which makes the infusion relatively stable.

Another embodiment of the present invention can also increase the frequency of the force output by the linear actuator 180 or by the reset unit 170 to increase the frequency or the rate of the reciprocating rotation of the driving member 150, thereby increasing the infusion rate of the infusion device.

In addition, the infusion devices of other embodiments of the present invention can change the driving power output frequency of the linear actuator 180 or the reset unit 170, which makes infusion device have multiple infusion rates. Here, the change of the driving power output frequency of the linear actuator 180 or the reset unit 170 can change the rate of any single movement, the rate of the reciprocating movement, or the frequency of the reciprocating movement of the driving member 150.

Figure 8A:
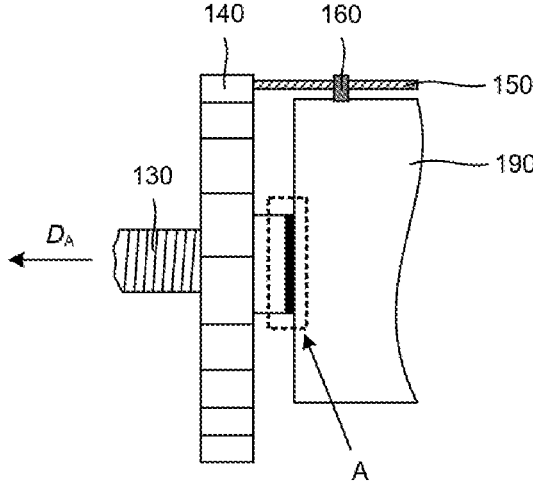
FIG. 8*a* and FIG. 8*b* are schematic diagrams of the driving wheel and the base, or the position limited member according to an embodiment of the present invention.
Figure 8B:
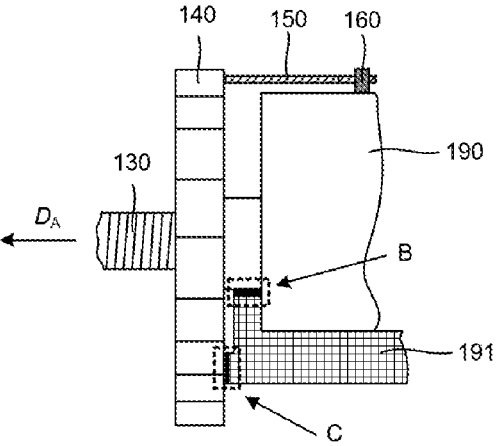

FIG. 8a and FIG. 8b are schematic diagrams of the driving wheel 140 and the base 190, or the position limited member 191 according to an embodiment of the present invention. FIG. 8a and FIG. 8b are front views of FIG. 3c.

When the driving end 151 slides on the surface of the wheel teeth 141, the driving end 151, contact with the wheel teeth 141, applies a certain pressure to the driving wheel 140 to ensure the non-rotating of the driving wheel 140. However, it is obvious that due to the structural features of the wheel teeth 141 and the circumference of the driving wheel 140, the pressure applied by the driving end 151 is not equal at different positions. Therefore, when the driving end 151 slides (including reset movement or sliding forward) on the surface of the wheel teeth 141, the driving wheel 140 may rotate forward or reverse, which affects the accuracy of the drug infusion volume and brings safety risk.

As shown in FIG. 8a, the driving wheel 140 is movably assembled on the base 190 remaining in frictional engagement. Here, the friction fit between these two means a certain friction force preset between two mutually moving components, so as to the meaning of the following friction fit. In the embodiment of the present invention, the frictional force of the relative movement between the driving wheel 140 and the base 190 is applied or increased at the position A, indicated by the dotted frame, to ensure that when the driving end 151 slides on the surface of the wheel teeth 141, the driving wheel 140 stops rotating.

As shown in FIG. 8b, in another embodiment of the present invention, the infusion device further includes a position limited member 191 that is movably assembled on the base 190 to limit the position of the driving wheel 140. The position limited member 191 is in friction fit with the driving wheel 140 at position B or position C, indicated by the dotted frame. Similarly, in the embodiment of the present invention, the position limited member 191 increases the frictional force that the driving wheel 140 receives when rotating, also ensuring that the driving wheel 140 stops rotating when the driving end 151 slides on the surface of the wheel teeth 141. At the same time, the position limited member 191 can make full use of the internal space of the infusion device, and frictionally cooperate with the driving wheel 140 at multiple positions.

Other embodiments of the present invention do not limit the position of the above friction fit, as long as the condition for applying or increasing the friction force received by the second driving unit during movement is satisfied. For example, the friction force can also be applied on both sides of the driving wheel 140 at the same time. The embodiment of the present invention neither limits the material of the position limited member 191. For example, the position limited member 191 is an elastic member, a plastic member or a metal member.

Other embodiments of the present invention may increase the pressure of the driving end 151 on the wheel teeth 141 instead of providing the above-mentioned friction fit, which can increase the maximum static friction of the driving wheel 140 and also ensure the non-rotating of the driving wheel 140 when the driving end 151 slides on the surface of the wheel teeth 141.

Figure 9:
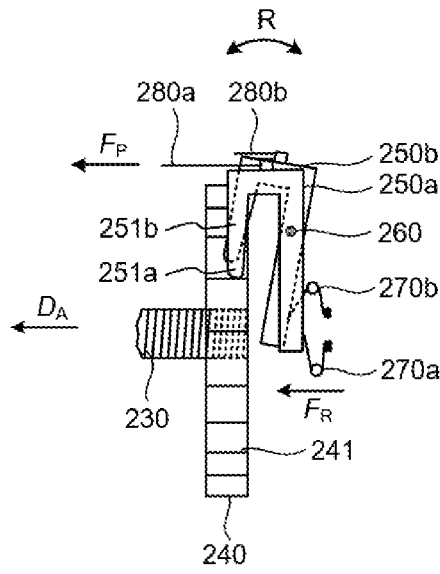
FIG. 9 is a schematic diagram of a driving unit including two driving members according to an embodiment of the present invention.
Figure 10:
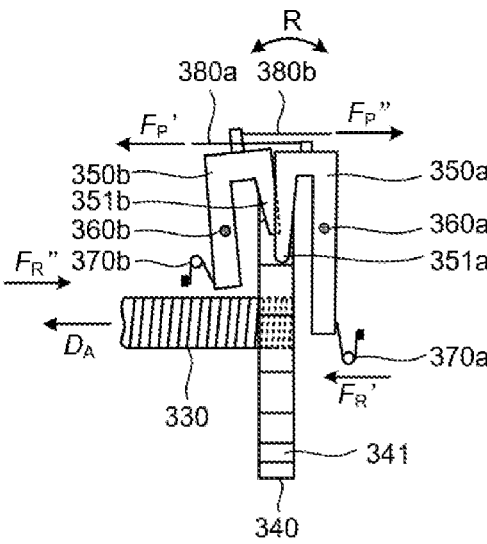
FIG. 10 is a schematic diagram of a driving unit including two driving members according to another embodiment of the present invention.

FIG. 9 and FIG. 10 are schematic diagrams of a driving unit including two driving members according to different embodiments of the present invention.

As shown in FIG. 9, the driving member 250a rotates reciprocally in the R direction around the rotating shaft 260 under the action of the linear actuator 280a and the reset unit 270a. Similarly, the driving member 250b rotates reciprocally in the R direction around the rotating shaft 260 under the action of the linear actuator 280b and the reset unit 270b. In the embodiment of the present invention, the reciprocating rotations of the two driving members do not interfere with each other. Therefore, both the driving member 250a and the driving member 250b can independently implement the driving method or principle described above.

Preferably, in the embodiment of the present invention, the driving member 250a and the driving member 250b rotate asynchronously. That is, when the driving end 251a of the driving member 250a pushes the wheel teeth 241 to move, the driving end 251b of the driving member 250b slides on the surface of the wheel teeth 241. When the driving end 251b slides to one position, the control unit controls the linear actuator 280a to stop outputting driving power to the driving member 250a, and in turn controls the linear actuator 280b to output power to the driving member 250b. At this time, the driving member 250a rotates in the clockwise direction under the action of the reset unit 270a, and the driving end 251a slides on the surface of the wheel teeth, while the driving end 251b pushes the wheel teeth 241. The driving members 250a and 250b are alternately powered to push the driving wheels 240.

In the embodiment of the present invention, the pulling force $F_P$ of the linear actuators 280a and 280b, the elastic force $F_R$ of the reset units 270a and 270b and the forward direction $D_A$ of the screw 230 are shown in the figures. Like foregoing statement, the direction of the pulling force $F_P$ is parallel to the forward direction $D_A$ of the screw 230.

In the embodiment of the present invention, the types of the reset units 270a and 270b can be referred to the above, which will not be repeated herein.

As shown in FIG. 10, the driving ends 351a and 351b alternately push the wheel teeth 341, respectively, and the power output by the linear actuators 380a and 380b are both controlled by the control unit 101.

It should be noted that, in the embodiment of the present invention, the direction of the pulling force $F_P'$ of the linear actuator 380a and that of the pulling force $F_P''$ of the linear actuator 380b are opposite. Obviously, the direction of the resetting force $F_R'$ of the reset unit 370a and that of the resetting force $F_R''$ of the reset unit 370b are also opposite.

Also, in the embodiment of the present invention, the driving members 350a and 350b rotate asynchronously. That is, when the driving end 351a of the driving member 350a pushes the wheel teeth 341 to forward, the driving end 351b of the driving member 350b slides on the surface of the wheel teeth 341. When the driving end 351b slides to one position, the control unit controls the linear actuator 380a to stop outputting power to the driving member 350a, and in turn controls the linear actuator 380b to output power to the driving member 350b. The driving member 350a resets to the clockwise rotation by the reset unit 370a, while the driving end 351a slides on the surface of the wheel teeth 341, and the driving end 351b pushes the wheel teeth 341. The driving members 350a and 350b alternately pushes the driving wheels 340.

Similarly, both the driving member 350a and the driving member 350b can independently implement the driving method or principle described above. And the types of the reset units 370a and 370b can be referred to the above, which will not be repeated herein.

It should be noted that, in other embodiments of the present invention, more driving members can be arranged in the driving unit, or more driving ends are disposed on each driving member, or more driving wheels can also be provided in the infusion device. Therefore, different driving members respectively push the corresponding driving wheels to rotate.

FIG. 11a and FIG. 11b are schematic diagrams of two driving ends 451a and 451b of a driving member 450 cooperating with two driving wheels 440a and 440b respectively according to yet another embodiment of the present invention. FIG. 11b is a right view of the partial teeth component of the driving wheels 440a and 440b in FIG. 11a.

As shown in FIG. 11a and FIG. 11b, in the embodiment of the present invention, the driving member 450 includes two driving ends 451a and 451b disposed left and right, while two fixedly connected driving wheels 440a and 440b also disposed on the left and right (that is, two driving wheels can move simultaneously). The driving ends 451a and 451b cooperate with the driving wheels 440a and 440b, respectively, and the rotating shaft 460 is disposed on the same side of two driving wheels 440a and 440b. Both the linear actuator 480 and the reset unit 470 of the embodiment of the present invention are shape memory alloys, and the driving end 451a or 451b can respectively push the wheel teeth 441a or 441b forward. Their working principles and operating modes are consistent with the foregoing embodiments.

In addition to driving end 451a or 451b operating independently, the embodiment of the present invention can also adjust the distance between the front ends of the driving ends 451a and 451b, or adjust the offset degree of the wheel teeth 441a and 441b to make two driving ends 451a and 451b cooperate with each other. Preferably, in the embodiment of the present invention, the wheel teeth 441a and 441b are offset with degree t, as shown in FIG. 11a and FIG. 11b. The following teeth offset of two driving wheels have the same meaning here.

Obviously, in the embodiment of the present invention, two driving ends 451a and 451b reciprocate synchronously. As shown in FIG. 11a, when the previous forward movement is completed, the driving member 450 starts a reset movement, the driving end 451a reaches the driving position before the driving end 451b, so the driving end 451a can be used to start the next forward movement instead. Or the driving member 450 continues the reset movement until the driving end 451b reaches the next driving position to start the next forward movement. Of course, the driving member 450 may continue to be reset for a much larger distance, as described above. Here, the driving position refers to the position where the driving end can push the wheel teeth forward, as shown in the positions $E_1$ and $E_2$ in FIG. 7, and the following driving position has the same meaning as here.

Therefore, by controlling the rotation amplitude of the driving member 450, the driving end 451a or 451b can individually push the corresponding wheel teeth 441a or 441b forward, or the driving end 451a or 451b alternately pushes the wheel teeth forward, making the infusion device have multiple infusion increments.

FIG. 12a and FIG. 12b are still another embodiment of the present invention in which the driving member 550 includes two driving ends 551a and 551b disposed up and down, and driving ends 551a and 551b cooperate with the same driving wheel 540. FIG. 12b is a perspective diagram of the driving member 550 in FIG. 12a.

As shown in FIG. 12a and FIG. 12b, the driving member 550 includes two driving ends 551a and 551b disposed up and down cooperating with the same driving wheel 540, so the driving ends 551a and 551b reciprocate synchronously. The front ends of the driving ends 551a and 551b are not level with a certain distance m, therefore, the two cannot simultaneously push the wheel teeth 541 forward, as shown in FIG. 12a. When the driving end 551b finishes the last forward movement, the driving member 550 performs a reset movement, obviously making the driving end 551a reach the next driving position before the driving end 551b. The driving end 551a can be used to push the wheel teeth 541 forward to start the next forward movement. Or the driving member 550 continues the reset movement until the driving end 551b reaches the next driving position to start the next forward movement. Of course, the driving ends 551a and 551b can also reset to a much larger distance, as described above.

Therefore, by controlling the power output by the linear actuator 580 or the reset unit 570, the driving member 550 has different rotation amplitudes, which makes the driving end 551a or 551b individually push the wheel teeth 541 forward or the two alternately push the wheel teeth 541 forward, thereby making the infusion device have a variety of different infusion increments.

In other embodiments of the present invention, the driving member may further include more driving ends, such as 3, 4 or more, which is not specifically limited herein.

When the drug infusion device has multiple infusion modes, the user, according to the actual requirements, can flexibly select the infusion mode to stabilize the level of body fluid parameters. Taking insulin stabilizing blood glucose levels as an example, some users or body tissues at the infusion site absorb insulin slowly. Users can choose an infusion mode with smaller infusion increment or lower infusion rate, which not only stabilizes the blood glucose level, but also improves the utilization of insulin, reducing the burden on body tissues. As another example, blood glucose spikes after a meal, so the user can first select an infusion mode with a relatively large infusion increment or a relatively high infusion rate to suppress the rapid rise in blood glucose, and then select an infusion mode with a medium infusion increment or infusion rate, and finally, choose an infusion mode with a relatively small infusion increment or a relatively low infusion rate to slowly stabilize blood glucose at a reasonable level. For another example, the bolus insulin required after each meal is different, and the body's basal insulin requirement is also different at different periods of one day. Therefore, multiple infusion modes of the infusion device can be flexibly selected (by the user or automatically by the closed-loop system) according to the actual requirements to achieve the goal of precise control of blood glucose levels.

In summary, the unilaterally driven drug infusion device disclosed in the present invention, provided with at least two blocking walls, can precisely control the rotation amplitude of the driving member so that the minimum infusion amount is at least ½ unit infusion amount, which improve the infusion accuracy of the infusion device. The user or the closed-loop system can flexibly select different infusion modes to precisely control the body fluid level to meet the needs of the body, improving user experience.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A unilaterally driven drug infusion device, comprising:
a reservoir, a piston and a screw, the piston connected with the screw and arranged in the reservoir;
a driving unit comprising at least one rotating shaft and at least one driving member, wherein the driving member includes at least one driving end, and the driving member rotates around the rotating shaft to advance or reset the driving end;
at least one driving wheel provided with wheel teeth, the driving end which advances pushes the wheel teeth to rotate the driving wheel, thereby driving the screw forward;
a linear actuator and a reset unit respectively connected to the driving member, wherein the linear actuator and the reset unit respectively apply driving power to the driving member to advance and reset the driving end; and
at least two first blocking walls, arranged at one side of the driving unit to limit an advancing position of the driving unit,
wherein when the driving member is in a first position, the driving member does not contact the first blocking walls, when the driving member is in a second position, the driving member contacts one of the first blocking walls, when the driving member is in a third position, the driving member contacts another one of the first blocking walls.

2. The unilaterally driven drug infusion device of claim 1, wherein each of the first blocking walls is an elastic conductive member.

3. The unilaterally driven drug infusion device of claim 2, wherein the elastic conductive member comprises a conductive spring, a conductive leaf spring, a conductive rubber, or conductive silica gel.

4. The unilaterally driven drug infusion device of claim 1, wherein the linear actuator comprises an electrically driven linear actuator or an electrically heated linear actuator.

5. The unilaterally driven drug infusion device of claim 1, wherein the reset unit comprises an electrically driven linear actuator or an electrically heated linear actuator.

6. The unilaterally driven drug infusion device of claim 5, wherein at least a second blocking wall is arranged on an other side of the driving unit.

7. The unilaterally driven drug infusion device of claim 6, further comprising a control unit, jointly control a moving end position of the driving member with the second blocking wall on the other side of the driving unit.

8. The unilaterally driven drug infusion device of claim 1, wherein the reset unit is an elastic member, the elastic member at least comprises a spring, an elastic piece, an elastic plate, an elastic rod, or rubber.

9. The unilaterally driven drug infusion device of claim 8, wherein the reset unit is an elastic conductive member.

10. The unilaterally driven drug infusion device of claim 9, wherein the elastic conductive member comprises a metal spring or a conductive rubber.

11. The unilaterally driven drug infusion device of claim 1, wherein the driving member comprises a plurality of operating modes, thereby making the infusion device have a plurality of infusion increments or infusion rates.

12. The unilaterally driven drug infusion device of claim 11, wherein the operating modes of the driving member comprise different amplitudes of reciprocating movements, frequencies of reciprocating movements or different movement rates.

13. The unilaterally driven drug infusion device of claim 1, further comprising a base on which the driving wheel is movably assembled, wherein the base and the driving wheel are frictional fit, and the driving wheel stops rotating when the driving end is sliding on a surface of the wheel teeth.

14. The unilaterally driven drug infusion device of claim 13, further comprising s a position limited member which is movably assembled on the base to limit a position of the driving wheel, wherein the position limited member and the driving wheel are frictional fit, and the driving wheel stops rotating when the driving end is sliding on the surface of the wheel teeth.

* * * * *